United States Patent [19]
Dempster et al.

[11] 4,155,246
[45] May 22, 1979

[54] RAPID GAS ANALYZING SYSTEM

[75] Inventors: Philip T. Dempster; John Y. Pun, both of St. Helena, Calif.

[73] Assignee: Harley E. Schear, San Francisco, Calif.

[21] Appl. No.: 787,156

[22] Filed: Apr. 13, 1977

[51] Int. Cl.[2] ............................................. G01N 29/02
[52] U.S. Cl. ......................................................... 73/24
[58] Field of Search ........................... 73/24; 324/83 A

[56] References Cited

U.S. PATENT DOCUMENTS 2,984,097  5/1961  Kniazuk et al. ............................. 73/24

FOREIGN PATENT DOCUMENTS 1302380  1/1973  United Kingdom ......................... 73/24

OTHER PUBLICATIONS

Staffin; "6 Ways to Measure Phase Angle", *Control Engineering*, Oct. 1965, pp. 78–83.
Abello; "Absorption of Ultrasonic Waves by Various Gases", *Physical Review*, vol. 31, Jun. 1928, pp. 1083–1090.

*Primary Examiner*—Stephen A. Kreitman
*Attorney, Agent, or Firm*—Robert B. Block

[57] ABSTRACT

Gas analyzing system using sonic wave shift over tubular gas column. Reference gas passed through column calibrates system to zero reference level. Sample gas having unknown amount of known gas component causes shift of wavelength distance in column. Phase comparator looks at shifted signal over ±90° of phase shift. Integrator responds to comparator output to give dc output signal proportional to phase shift. Compensating circuits in final amplifier estimate probable final value based on rate of change of initial comparator output and use same to drive output meter.

8 Claims, 3 Drawing Figures

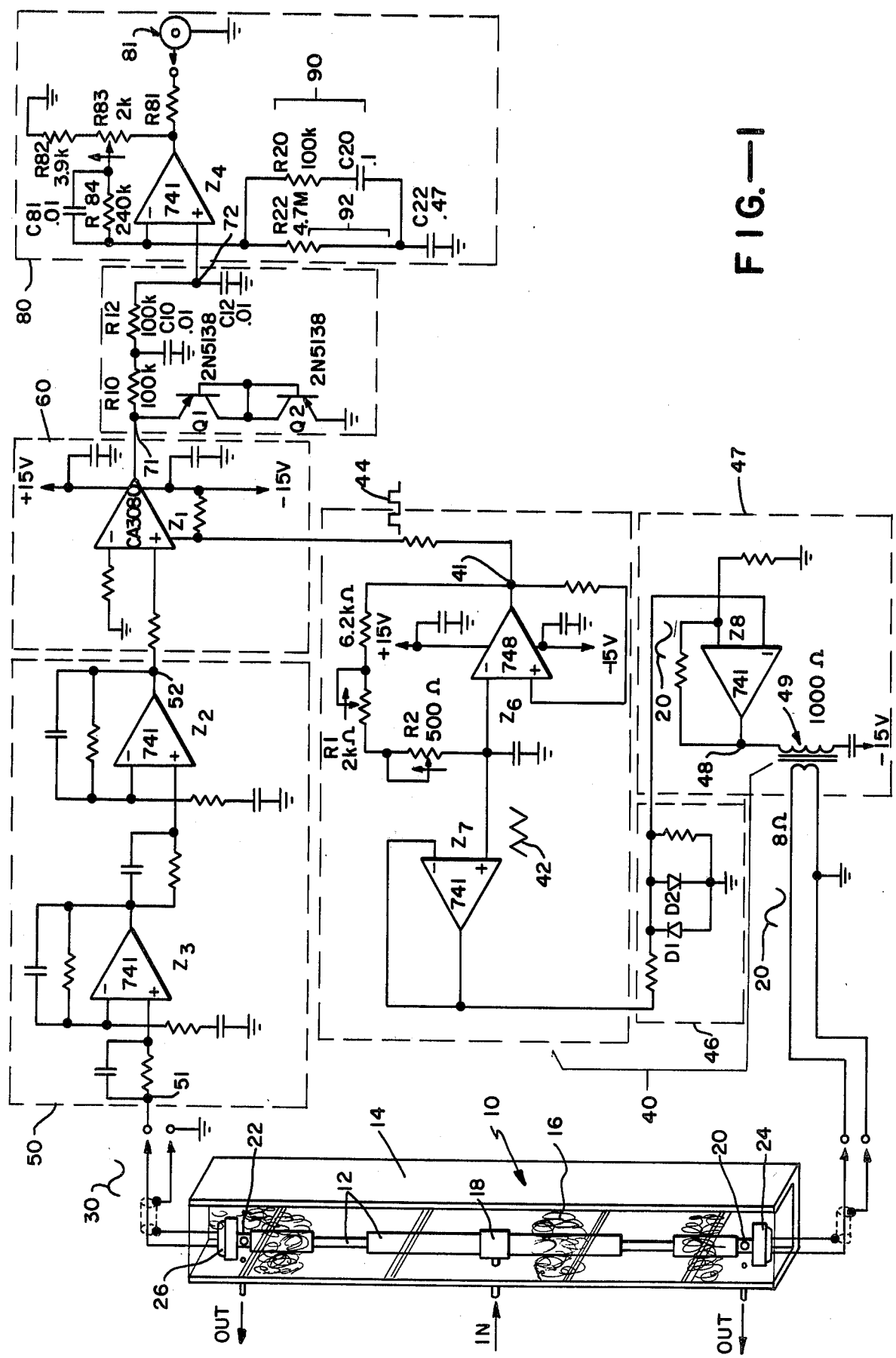
FIG.—1

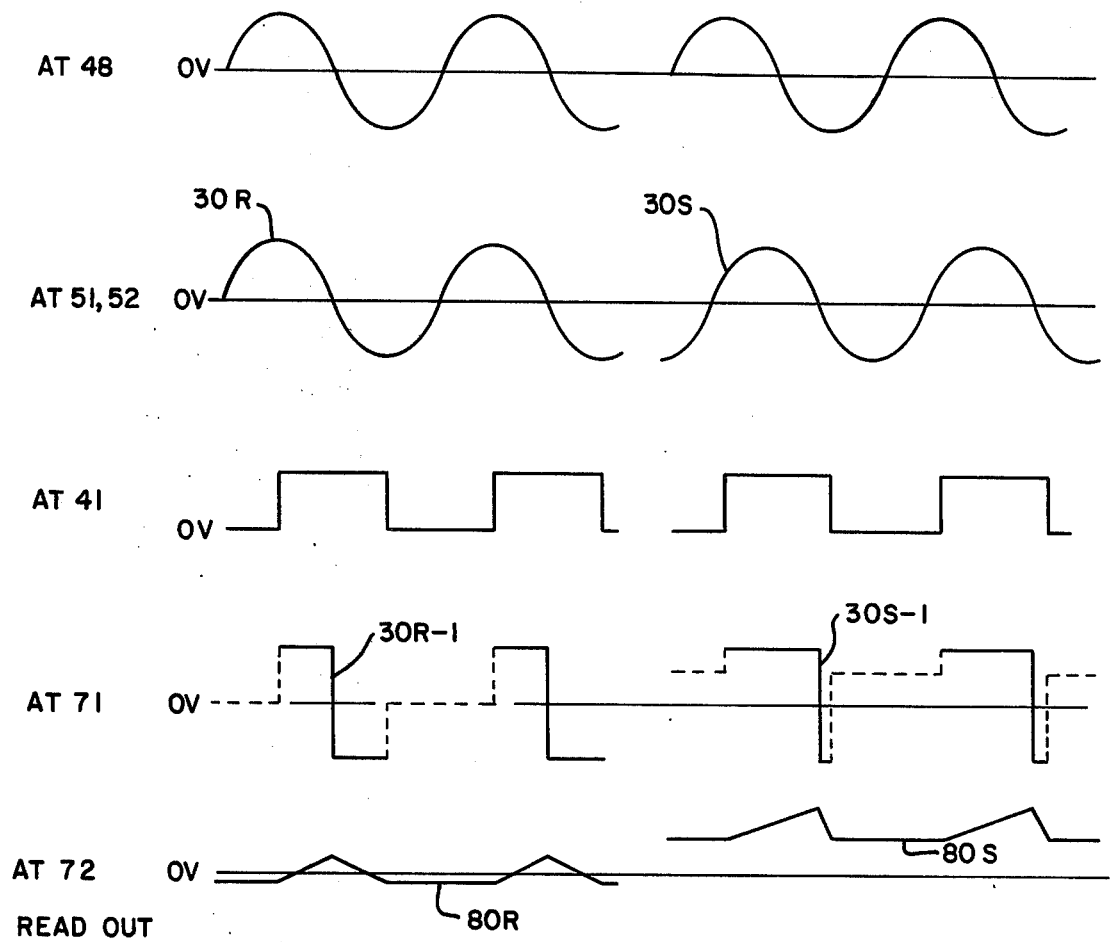
FIG.—2
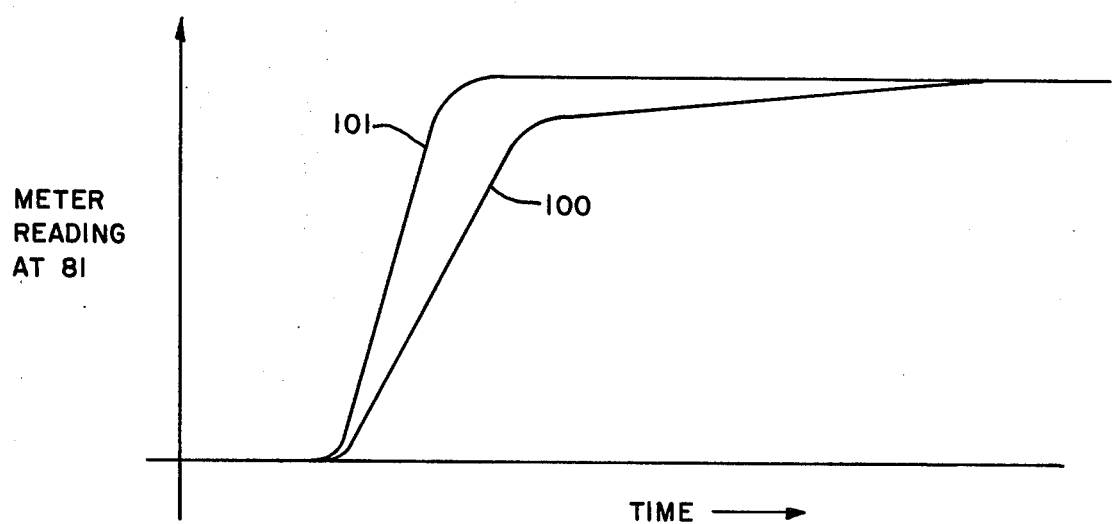
FIG.—3

RAPID GAS ANALYZING SYSTEM

BACKGROUND OF THE INVENTION

This invention relates to gas analyzing systems and especially such systems wherein it is desired to determine quantitative values of a mixture of gases. Applications of such systems include respiratory function measurements in the medical field wherein a pulmonary function is evaluated such as in the measurement of total lung volume, as distinguished from residual or useful volume, and, in the measurement of oxygen carbondioxide respiratory exchange.

The principles upon which the present invention is an improvement are known and is based on the differing sonic velocities of a sound wave in different gaseous mixtures. As is known, the speed of sound in air versus the speed of sound in a mixture of air and another gas component can differ by a substantial amount. For example, if a sonic standing wave pattern is established through a column containing a mixture of helium in air, a corresponding difference in basic wave-length is established and can be measured electronically.

Advantage taken of these differences in the speed of sound through varying mixtures in the present invention to develop a rapidly readable, analog output signal by use of rapid acting electronic signal processing circuits.

In one form of known apparatus described in U.S. Pat. No. 2,984,097 issued May 16, 1961 to Michael Kniazuk a large number of standing waves (200-600) were established in a column in a tube having a transmit transducer coupled at one end and a receive transducer coupled at the other end. The shift in wave length caused by introducing a gaseous mixture different from a reference gas was manually counted by visually reading the number of 360° or 180° phase inversions of a Lissajous figure displayed on an oscilloscope trace. Additional fine reading was obtained by manually adjusting a phase shift capacitor in an associated circuit to bring the Lissajous figure to the nearest nul value after which the unknown amount of the gas introduced into the mixture is determined by adding the manually derived count from the oscilloscope trace to the manually derived shift in phase caused by the manually adjustable capacitor. Thus, the capacitance of phase shift and total number count of scope inversions provided in that system a measure of the unknown amount of gas. Such a procedure is inherently slow, is time-consuming of operator time and is entirely manual and therefore subject to operator error. There is, therefore, a need for a new and improved gas as an analyzing system.

SUMMARY OF THE INVENTION AND OBJECTS

In general it is an object of the present invention to provide a rapid automatically reading gas analyzing system which will overcome the above limitations and disadvantages.

It is the further object of the invention to provide a non-operator controlled system of the above character for displaying an analog output measuring on a calibrated meter for indicating the amount of a component concentration in the gaseous mixture.

Another object of the invention is to provide a gas analyzing system of the above character the output of which is in an electrical signal analog form which is easily converted by electronic circuits into a digitized form capable of transmission over telephone or radio circuits.

Another object of the invention is to provide a gas analyzing system of the above character which is easily calibrated to a zero reference and which is particularly rapid in read-out based upon estimations of final value derived from initial signal phase shift.

The present invention uses a low sonic frequency wave in a tube forming a gas column having a length equal to an integral low number of one-half ($\frac{1}{2}$) wave lengths of a reference gas in length. Preferably, the wave length is one (1) wave length but may be anywhere from one half wave length to as much as three or four wave lengths. A convenient tube length for forming the column is found at one (1) wave length to be approximately 5-6 inches in length for sonic waves of about 3.5 kilohertz for aid. A sinusoidal oscillator delivers a signal and drives a transmit transducer at one end of the tube while a receive transducer senses the output at the other end of the tube which output lags the input by a predetermined amount such as by one wave length. The resulting sinusoidal output is amplified and its sign sampled over a time interval of one-half cycle in length and applied to a comparator gated by the oscillator to develop a $\pm k$ sampled signal depending upon the sign of the input. The average value of the sampled signal $\pm k$ is developed by an integrator circuit to form an incompensated output signal. If, for example, using a half wave length measurement the time interval is integrated from peak positive to peak negative for a reference gas, the resulting output will be the average or zero. Any phase shift in wave length introduced by the introduction of an unknown amount of a component gas to the reference will cause a shift in the wave length and this will appear as an electrical phase shift towards more positive or negative integrated values of the sampled signal $\pm k$, compared with balanced, "zero" reference value. The integrated result will be an output value differing from "zero" reference by an amount which is a proportional and increasing function of the amount of shift. This analog output signal in integrated form is directly readable by a suitably calibrated meter. A particularly useful speed-up circuit is incorporated in the circuitry of the present invention which enables highly reliable estimated output readings to be made almost immediately. These estimated output readings are electronically derived and are based upon calculations of final value as related to rate of change in the initial shift upon introduction of the unknown amount of component gas to be measured.

These and other features and advantages of the present invention will become apparent from the following description and claims when taken together with the accompanying drawings, of which:

DESCRIPTION OF THE PREFERRED EMBODIMENT

FIG. 1 is a schematic drawing of the gas analyzing apparatus of the present invention.

FIG. 2 is a graph showing portions of the output wave plotted in time against the sampling pulse as a result of measuring reference and unknown gaseous samples and the integrated value thereof.

FIG. 3 is a graph plotting output response for incompensated and compensated signals.

DETAILED DESCRIPTION OF THE PREFERRED EMBODIMENTS

Referring now to FIG. 1 there is shown in schematic form an embodiment of the present invention particularly adapted for the measurement of total lung capacity. Commonly, such capacity uses a reference gas consisting of ambient air and a sample gas consisting of 10% helium and 90% air which has been exhaled by a patient.

In general, the invention as shown in FIG. 1 consists generally of means 10 forming an elongate sample tube 12 forming a gas column for receiving gases through which a sonic wave is passed to establish a standing wave pattern. This tube is approximately a low integer number of half wave lengths long for the reference gas. In the case of air and in the preferred embodiment shown, the tube is about one wave length long at a frequency of operation of approximately 3.5 kHz or about 5 to 6 inches long. The tube itself is constructed of a suitable flexible material resistant to passage of sonic waves therethrough such as rubber or other elastomer and may comprise an equal internal diameter tube or several sections some of which may have differing internal diameters to provide a longer effective wave length, as shown. The tube is encased within a thermally stable environment such as a thermally conductive U-shaped channel 14 maintained at a constant temperature and is packed therein within sound-absorbing material 16 to further prevent stray sound radiation from affecting its operation. The reference gas and sample gas are fed to the tube through a T-section 18 formed at its mid-point and is removed from the tube through output ports 20, 22 taken from the ends thereof in the manner to be described. Thus, the end of the tube is terminated in the nipple-like extension of a transmit transducer 24 which may be an electromagnetic plug like earphone of the type commonly used on portable radios, the input to which is an electronic signal. The output of transducer 24 is an acoustic wave which passes through the tube 12 and is received by an identical transducer 26 (electromagnetic earphone) at the other end of tube 12 which converts the sonic wave into an electronic output signal 30. The nipple sections 20, 22 of the earphone transducers are preferably drilled with a small (20/1000 of an inch) hole and a negative pressure maintained thereon so as to withdraw gases passing through the tube at a controlled rate.

Means 40 are provided for developing an input drive signal and consists of operational amplifier Z6 connected in a usual oscillator configuration consisting of a negative feedback loop with lag and a positive feedback loop but without lag such that two outputs are developed, the first output 42 taken from the negative terminal of Z6 is of triangular form while the second output 44 is taken to the gate input of Z1 is of square wave form 90° out of phase with triangular first output. The frequency of operation is adjusted by varying course and fine controls on variable resistors R1, R2, respectively, incorporated in series in the negative feedback loop. The triangular wave is passed through amplifier Z7 serving as a buffer amplifier to the input of a non-linear diode network 46 which converts the triangular wave into a roughly sinusoidal wave which is delivered to an isolation and amplifier 48 including operational amplifier Z8 the output of which is taken through an impedance transformer 49 to the transmit earphone transducer 24.

The electronic output signal 30 of the receive transducer is taken through amplifier stage 50 including a pair of identical amplifiers Z3 and Z2 connected in tandem to supply sufficient gain to operate the remainder of the apparatus. The output of the amplifier section is taken to the positive input of comparator stage 60 consisting of an operational amplifier Z1. The gate control of which is connected to the square wave output of oscillator Z6. Because of the 90° phase shift between the outputs of the oscillator, the second output, when used as a gate, will turn the comparator "on" at the peak positive excursion of the received sine wave signal and turn the same off at the next peak negative excursion. Thus, the comparator output is positive for a quarter cycle and negative for a quarter cycle each being an equal length of time under reference conditions. Accordingly, the output of Z1 can be expressed as a square wave, voltage limited by the network Q1, Q2 consisting of transistors connected to form the equivalent of back-to-back Zener diodes), and has an average minimum value, defined as "zero," because of the equal positive and negative excursions. The output of Z1 appears through 100K resistors R10 and R12 and across capacitors C10 and C12 connected in a pi network and to filter out ripple. The output of the sample comparator circuit at 71 is taken to a variable response final amplifier 80 having an adjustable feedback loop R82, R83, R84, C81 which provides for change in scale factor of the output developed. The feedback loop is tied to a compensating network R92, C27, R20, C22 as will be discussed.

Referring now to FIG. 2, the operation of the foregoing circuits will be discussed in greater detail with reference to the graphs shown. Thus, during passsge of a reference gas, the reference output signal 30 is adjusted in relative position to the square wave output of the oscillator by adjusting the frequency of operation of the oscillator. This is easily accomplished by adjustment of course control variable resistor R1 and and fine control variable resistor R2. After such adjustment the maximum positive excursion of the signal 30R occurs at the same time, T1, as the leading edge of the square wave pulse rising and the maximum negative excursion occurs at the same time T2 as the negative going excursion of the square wave. The resulting output signal 30R-1 appears in heavy lines traced in FIG. 2. Thus, during the initial reference period, when the comparator is on, it sees a positive quarter wave and a negative quarter wave at its input and the output swings positive and negative for equal lengths of time as shown in 30R-1. The output then, expressed as a current, voltage limited by Q1, Q2 is elevated to values of plus or minus approximately 7 volts per swing. Since the swing is symmetrical, the capacitance resistance network R10 C10; R12 C12 following the output of Z1 receives equal charge during each period of time so that its average value assumes a low base-line level, defined as the "zero" level. Whenever the Z1 is gated off by the square wave, it forms an open circuit and therefore whatever of value previously appeared across capacitors C10 and C12 remains during the off cycle. When the sample gas is introduced through the tube a phase shift between the signals occurs due to the differing wave lengths of the sample gas containing the unknown component compared to the reference gas. This is indicated schematically in FIG. 2 by signals 30-S which have been shifted to the right by nearly 90°. The resultant sample pulse 30-S is nearly altogether positive as may be seen and therefore the value of a current available for charging capacitors C10 and C12 is nearly a maximum, and such capacitors become charged up to a predetermined level, the magnitude of which is dependent upon the relative amounts of positive and negative going comparator output excursions passed by the gate comparator Z1 which in turn is proportional to the amount of phase shift and thus the amount of the unknown component in the sample gas. In FIG. 2, graphs 30R-1 and 30S-1 illustrate the output sample signals at 71. Readout signals 80-R and 80-S illustrate the resultant at 72. Signals 80-R and 80-S are averaged by the meter response time to give a steady reading at 81.

The output amplifier compensation network 80 as provided consists of two sections 90, 92 connected across the feedback loop of operational amplifier Z4. The first section 90, including R20, C20, and C22 has a short time constant T-1 which compensates for the time it takes to fill the sample tube while the other R22, C22 has a relatively long-time constant which compensates for the time it requires for a change of gas sample from reference to sample gas to diffuse into the space of the earphones. Without compensation by these circuits, the output shifts rapidly to 95% of its final value but then shifts much more slowly toward the final value as shown in graph 100 of FIG. 3. These compensating circuits initially speed up the response time by estimating the final value based on the initial rate of change and prediction of the probable final value. These circuits can be said to estimate by the rate of change that the gas must have a phase shift value of a certain predetermined amount for that magnitude of change. The result is that the output shifts rapidly to the probable final value as shown by graph 101 by the addition of a 5% overshoot during an initial time T-1 and holds that value for later substantiation as the current drawn through R10 and R12 and the charge on capacitor C12 stabilizes. Thus, R20, C20, and C22 increase the speed at which the value appearing across of signal across C12 is delivered as an output and the resultant overshoot slowly decays through second section 92, including R22 and C22, so that the output is stabilized. The decay time constant T-2 of section 92 is long enough to permit the reference or sample gas to diffuse through the transmit and receive transducers.

To those skilled in the art to which this invention pertains, many modifications and adaptations of the same will occur. For example, while the present invention has been disclosed and illustrated with respect to its use in connection with a gaseous unknown component consisting of helium in which the wave passage through the sample gas is speeded up to develop an output signal of a predetermined polarity it will be understood that other unknown gas components may be introduced which will slow down the passage of the waves through the column and that such gas components may be measured by the identical apparatus, the output of which will merely be reversed in sign. Accordingly, the scope of the present invention should be taken in a broad sense and limited only by that of the accompanying claims.

What is claimed is:

1. In a method for rapid gas analysis the steps of establishing a standing wave pattern of sonic waves in a column and measurement of phase shifts caused by introduction of an unknown amount of a component of a gas into said column, the improvement comprising the steps of introducing a reference gas or gas mixture through said column, passing a sonic wave through said column, adjusting the frequency of said wave to a low integer number of half wave lengths of the length of said column, receiving an output signal from the other end of said column, electronically sampling said output over a period including equal positive and negative excursions above a null point therein and processing the sampled output during gas passage to derive a reference or base signal level using a comparator-gate circuit driving an integrator, adjusting the frequency to exactly match the length of said column and reference gas so that the reference signal output is ± zero, subsequently introducing a gaseous mixture sample containing an unknown amount of a component gas through said column, said unknown component having a speed of sound value differing from that of said reference to thereby cause a change in the sonic wave length of said sample mixture compared to said reference, electronical sampling over the same period established by said reference, measuring the change in integrated output signal level and comparing the same to the reference value to thereby derive a positive or negative analog output which is proportional to the change in the unknown amount of component in said sample mixture and has a positive or negative sign in accordance with whether the unknown had a greater or lesser amount of the gas component being measutred.

2. Apparatus for rapid gas analysis comprising, means forming a tube having first and second ends, forming a gas sample column, the length of said tube being approximately that of an integral number of one-half wave length of a sonic wave to be applied between the ends thereof, means for selectively introducing reference and sample gases through said column, means forming a transmit transducer connected to one end of said column, means forming a receive transducer connected to the other end of said column, said transducers being capable of producing and receiving an electronic signal and a sonic wave transmitted through said tube, an electronic oscillator and waveshaper having a first sine wave output connected to said transmission transducer and a second output having a predetermined phase relationship to said sine wave output, means for receiving the output of said receive transducer and for amplifying the same to a useful level, gated comparator means connected to receive as one input the signal from said receive transducer and amplifier, and connected to receive and be gated by the second output of said oscillator to develop an output signal, means for adjusting the frequency of said oscillator so that said average comparator output signal during passage of a reference gas is zero, while the average magnitude of the output signal during passage of a sample gas is proportional to the phase shift introduced by said sample gas, and means for giving a DC analog output signal which is proportional to the average magnitude of said phase difference.

3. Apparatus for rapid gas analysis comprising means forming a tube having first and second ends, forming a gas sample column, the length of said tube being approximately that of an integral number of one-half wave length of a sonic wave to be applied between the ends thereof, means for selectively introducing reference and sample gases through said column, means forming a transmit transducer connected to one end of said column, means forming a receive transducer connected to the other end of said column, said transducers being capable of producing and receiving an electronic signal and a sonic wave transmitted through said tube, an electronic oscillator and waveshaper having a first sine wave output connected to said transmission transducer and a second output comprising a square wave signal varying 90° in phase from said sine wave output, means for receiving the output of said receive transducer and for amplifying the same to a useful level, gated comparator means for receiving said amplified output signal and being controlled by said square wave to be turned on whenever the square wave signal is above a predetermined signal level to establish a measuring period, means responsive to said gated comparator for developing a signal indicative and for detecting a phase difference between a reference value established during the passage of a reference gas and a sample value during the passage of a sample gas and for giving a DC analog output signal which is proportional to the value of said phase difference.

4. Apparatus for rapid gas analysis comprising, means forming a tube having first and second ends, forming a gas sample column, the length of said tube being approximately that of an integral number of one-half wave length of a sonic wave to be applied between the ends thereof, means for selectively introducing reference and sample gases through said column, means forming a transmit transducer connected to one end of said column, means forming a receive transducer connected to the other end of said column, said transducers being capable of producing and receiving an electronic signal and a sonic wave transmitted through said tube, an electronic oscillator and waveshaper having a first sine wave output connected to said transmission transducer and a second output having a predetermined phase relationship to said sine wave output, means for adjusting the output frequency of said oscillator until the output of said phase comparator reaches a zero value during the passage of a reference gas indicating the condition that the wave length through said reference gas is exactly one an integral number of one-half wave lengths for the frequency and tube length employed, means for receiving the output of said receive transducer and for amplifying the same to a useful level, gated comparator means for receiving said amplified output signal, means for detecting a predetermined phase difference between a reference value established during the passage of a reference gas and a sample value during the passage of a sample gas and means for giving a DC analog output signal which is proportional to the value of said phase difference.

5. Apparatus for rapid gas analysis comprising, means forming a tube having first and second ends, forming a gas sample column, the length of said tube being approximately that of an integral number of one-half wave length of a sonic wave to be applied between the ends thereof, means for selectively introducing reference and sample gases through said column, means forming a transmit transducer connected to one end of said column, means forming a receive transducer connected to the other end of said column, said transducers being capable of producing and receiving an electronic signal and a sonic wave transmitted through said tube, an electronic oscillator and waveshaper having a first sine wave output connected to said transmission transducer and a second output having a predetermined phase relationship to said sine wave output, means for receiving the output of said receive transducer and for amplifying the same to a useful level, gated comparator means for receiving said amplified output signal and for detecting a predetermined phase difference between a reference value established during the passage of a reference gas and a sample value during the passage of a sample gas and for giving a DC analog output signal which is proportional to the value of said phase difference, and means for sensing the rate of change of the output signal from said comparator when a sample signal is passed through said tube and for developing an output analog signal to overshoot to an estimated probable final value during the period preceding actual receipt of the stabilized comparator output.

6. Apparatus for rapid gas analysis comprising, means forming a tube having first and second ends, forming a gas sample column, the length of said tube being approximately that of an integral number of one-half wave length of a sonic wave to be applied between the ends thereof, means for selectively introducing reference and sample gases through said column, means forming a transmit transducer connected to one end of said column, means forming a receive transducer connected to the other end of said column, said transducers being capable of producing and receiving an electronic signal and a sonic wave transmitted through said tube; an electronic oscillator and waveshaper having a first sine wave output connected to said transmission transducer and a second output having a predetermined phase relationship to said sine wave output, means for receiving the output of said receive transducer and for amplifying the same to a useful level, gated comparator means for receiving said amplified output signal and for detecting a predetermined phase difference between a reference value established by adjusting the frequency of said oscillator during the passage of a reference gas to a sample value output during the passage of a sample gas, said gated comparator being connected to receive as one input the signal from said receive transducer and amplifier, and being connected to receive and be gated by the second output of said oscillator to develop an output signal the average magnitude of which is proportional to the phase shift introduced by said sample gas to thereby give a DC analog output signal which is proportional to the value of said phase difference.

7. In a method for rapid gas analysis the steps of establishing a standing wave pattern of sonic waves in a column and measurement of phase shifts caused by introduction of an unknown amount of a component of a gas into said column, the improvement comprising the steps of introducing a reference gas or gas mixture through said column, passing a sonic wave through said column said frequency of said wave being adjusted to a low integer number of half wave lengths of the length of said column, receiving an output signal from the other end of said column, causing said frequency to be adjusted to match the length of said column and reference gas, electronically sampling the output over 180° wave period, electronically processing the output during reference gas passage to derive a reference or base signal level using a comparator circuit to drive an integrator, subsequently introducing a gaseous mixture sample containing an unknown amount of a component gas through said column, said unknown component having a speed of sound value differing from that of said reference to thereby cause a change in the sonic wave length of said sample mixture compared to said reference, measuring the change in integrated output signal phase and comparing the same to the reference value to thereby derive an analog output which is proportional to the unknown amount of component in said sample mixture, electronically measuring the initial rate of change caused by the unknown sample component, electronically estimating the probable final value of the integrated output during such initial period, causing the output signal to be elevated during such initial period by an overshoot value to thereby cause the same to assume the probable final value during a period sufficiently long to allow for diffusion of the sample gas through the tube column and preceding receiving an actual comparator signal of such magnitude during such period and thereafter causing the decay of said overshoot value over a time frame long enough to allow for diffusion of the measured gas through the column.

8. Apparatus for rapid gas analysis comprising, means forming a tube having first and second ends, forming a gas sample column, the length of said tube being approximately that of an integral number of one-half wave length of a sonic wave to be applied between the ends thereof, means for selectively introducing reference and sample gases through said column, means forming a transmit transducer connected to one end of said column, means forming a receive transducer connected to the other end of said column, said transducers being capable of producing and receiving an electronic signal and a sonic wave transmitted through said tube, an electronic oscillator and waveshaper having a first sine wave output connected to said transmission transducer and a second output having a predetermined phase relationship to said sine wave output, means for receiving the output of said receive transducer and for amplifying the same to a useful level, gated comparator means for receiving said amplified output signal and for detecting a predetermined phase difference between a reference value established during the passage of a reference gas and a sample value during the passage of a sample gas and for giving a DC analog output signal which is proportional to the value of said phase difference, means for sensing the rate of change of the output signal from said comparator when a sample signal is passed through said tube and for developing an output analog signal to overshoot to an estimated probable final value during the period preceeding actual receipt of the stabilized comparator output, said last named means further providing rapid overshoot compensation during the period of sample gas diffusion through the column formed by the tube and a slow acting return compensation to allow for the sample gas to diffuse through the transmit and receive transducers.

* * * * *